United States Patent [19]
de Nanteuil et al.

[11] Patent Number: 5,652,246
[45] Date of Patent: Jul. 29, 1997

[54] PIPERIDINE COMPOUNDS

[75] Inventors: Guillaume de Nanteuil, Suresnes; Georges Remond, Versailles; Bernard Portevin, Elancourt; Jacqueline Bonnet; Emmanuel Canet, both of Paris, all of France; Graham Birrell, Edimburgh, Scotland

[73] Assignee: Adir et Compagnie, Courbevoie, France

[21] Appl. No.: 546,263

[22] Filed: Oct. 20, 1995

[30] Foreign Application Priority Data

Oct. 21, 1994 [FR] France .................... 94 12580

[51] Int. Cl.$^6$ .................. C07D 471/02; C07D 235/22; A61K 31/44; A61K 31/415
[52] U.S. Cl. .................. 514/300; 514/303; 514/316; 514/322; 546/118; 546/187; 546/191; 546/199
[58] Field of Search .................. 546/118, 187, 546/191, 199; 514/300, 303, 316, 322

[56] References Cited

U.S. PATENT DOCUMENTS

| | | | |
|---|---|---|---|
| Re. 34,203 | 3/1993 | Bagley et al. | 514/259 |
| 3,719,683 | 3/1973 | Robison et al. | 546/118 |
| 3,894,030 | 7/1975 | Janssen et al. | 546/199 |
| 4,110,333 | 8/1978 | Vandenberk et al. | 546/198 |
| 4,680,296 | 7/1987 | Manoury et al. | 514/259 |
| 4,791,120 | 12/1988 | Lin et al. | 514/326 |
| 4,791,121 | 12/1988 | Kudzma et al. | 514/326 |
| 4,897,401 | 1/1990 | Janssens et al. | 514/303 |

*Primary Examiner*—C. Warren Ivy
*Assistant Examiner*—Lyman H. Smith
*Attorney, Agent, or Firm*—The Firm of Gordon W. Hueschen

[57] ABSTRACT

The invention relates to the compounds of formula (I):

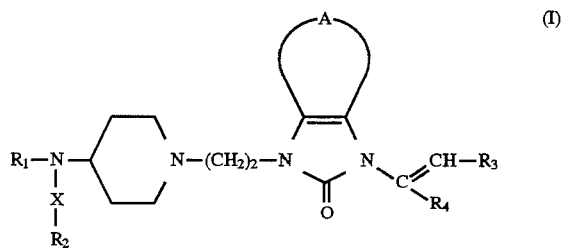

in which:

$R_1$ represents alkyl, phenyl, naphthyl, pyridyl or thienyl group, each phenyl, naphthyl, pyridyl or thienyl optionally being substituted, $R_2$ represents a hydrogen atom or a substituted or unsubstituted alkyl, substituted or unsubstituted phenyl, cycloalkyl, piperidino or substituted or unsubstituted amino group, X represents CO or $SO_2$, $R_3$ represents hydrogen or alkyl, $R_4$ represents alkyl, substituted or unsubstituted phenyl or trihalomethyl, or else $R_3$ and $R_4$ form, together with the carbon atoms which carry them, cyclo($C_3$–$C_7$)alkenyl, A represents phenyl, naphthyl or pyridyl ring, each phenyl, naphthyl or pyridyl ring optionally being substituted, their isomers, the corresponding quaternary ammonium salts of the piperidine and their addition salts with a pharmaceutically acceptable acid, an medicinal products containing the same are useful as antagonists of $NK_1$ receptors.

10 Claims, No Drawings

PIPERIDINE COMPOUNDS

BACKGROUND OF THE INVENTION

The present invention relates to new piperidine compounds.

1. Field of the Invention

The neurokinins form a family of neuropeptides having, at the C-end part, an analogous structure: Phe-X-Gly-Leu-Met. These neuropeptides, substance P (SP), neurokinin A (NKA) and neurokinin B (NKB), induce rapid contraction of smooth muscle fibers, as opposed to the slow contractions produced by bradykinin. Widely distributed in the human body, in particular in the central nervous system and in the peripheral nervous system, their endogenous agonist effects are exerted via specific receptors with a preferential affinity, for $NK_1$, $NK_2$ and $NK_3$ respectively, for SP, NKA and NKB. They are involved in many physiological or physiopathological processes, such as pain perception, vasopermeability, contractions of smooth muscle fibers, hypersecretions and modulations of the immune response (Otsuka M. et al., Physiol. Rev., 73,229–308, 1993).

The antagonist properties of the compounds of the invention with respect to neurokinin receptors and more particularly $NK_1$ receptors make it possible to use them in particular in the treatment of pain, inflammatory processes of various origins, gastrointestinal disorders, asthma, allergies, urological disorders, migraine and diseases of the central nervous system.

2. Prior Art Description

The closest compounds of the prior art are more particularly described in Patent EP 396,282, U.S. Pat. No. 4,791,121 or U.S. Pat. No. 4,791,120.

DETAILED DESCRIPTION OF THE INVENTION

The present invention more particularly relates to the compounds of formula (I):

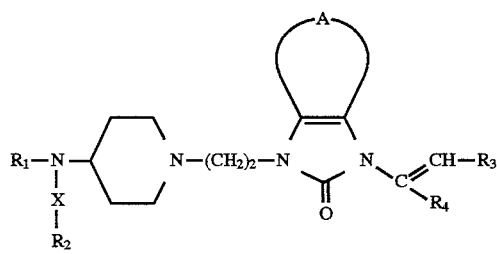

(I)

in which $R_1$ represents a linear or branched ($C_1$–$C_6$)alkyl, phenyl, naphthyl, pyridyl or thienyl group, each phenyl, naphthyl, pyridyl or thienyl group optionally being substituted by one or a number of halogen atoms or hydroxyl, linear or branched ($C_1$–$C_6$)alkoxy, linear or branched ($C_1$–$C_6$)alkyl, trihalomethyl or 1-hydroxy-2,2,2-trifluoroethyl groups, $R_2$ represents a hydrogen atom, a linear or branched ($C_1$–$C_6$)alkyl group (which is unsubstituted or substituted by one or a number of linear or branched ($C_1$–$C_6$) alkoxy or phenyl, amino or phthalimido groups), a phenyl group (which is unsubstituted or substituted by one or a number of halogen atoms or linear or branched ($C_1$–$C_6$)alkyl, linear or branched ($C_1$–$C_6$)alkoxy, hydroxyl or trihalomethyl groups), a cyclo($C_3$–$C_7$) alkyl group, a piperidino group or an amino group (which is unsubstituted or substituted by one or two linear or branched ($C_1$–$C_6$)alkyl groups), X represents a CO or $SO_2$ group, $R_3$ represents a hydrogen atom or a linear or branched ($C_1$–$C_6$)alkyl group, $R_4$ represents a linear or branched ($C_1$–$C_6$)alkyl group, a phenyl group (which is unsubstituted or substituted by one or a number of halogen atoms or linear or branched ($C_1$–$C_6$)alkyl, linear or branched ($C_1$–$C_6$)alkyl, hydroxyl or trihalomethyl groups) or a trihalomethyl group, or else $R_3$ and $R_4$ form, together with the carbon atoms which carry them, a cyclo($C_3$–$C_7$)alkenyl group, A represents, with the carbon atoms to which it is attached, a phenyl, naphthyl or pyridyl ring, each phenyl, naphthyl or pyridyl ring optionally being substituted by one or a number of halogen atoms or linear or branched ($C_1$–$C_6$)alkyl, linear or branched ($C_1$–$C_6$) alkyl, hydroxyl, amino, nitro or trihalomethyl groups, to their isomers, to the corresponding quaternary ammonium salts of the piperidine and to their addition salts with a pharmaceutically acceptable acid.

Mention may be made, among pharmaceutically acceptable acids, without implied limitation, of hydrochloric, hydrobromic, sulfuric, phosphonic, acetic, trifluoroacetic, lactic, pyruvic, malonic, succinic, glutaric, fumaric, tartaric, maleic, citric, ascorbic, oxalic, methanesulfonic and camphoric acids, and the like.

The quaternary ammonium salts of the piperidine can be produced, for example, using methyl iodide.

The invention also applies to the process for the preparation of the compounds of formula (I), which comprises the use, as starting material, of:

either an amine of formula (II):

(II)

in which $R_1$ has the same meaning as in the formula (I), which is reacted with a piperidone of formula (III):

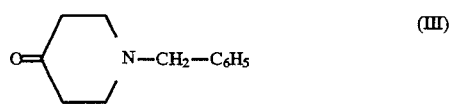

(III)

to lead to the compound of formula (IV),

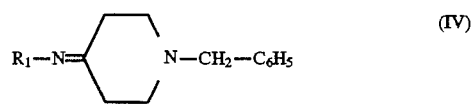

(IV)

in which $R_1$ has the same meaning as in the formula (I), which is reduced in the presence of a metal hydride, to lead to the compound of formula (V):

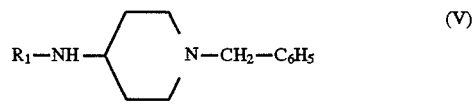

(V)

in which $R_1$ has the same meaning as in the formula (I), which is reacted with an anhydride, an acid chloride or phosgene (followed by reaction with a secondary amine), to lead to the compound of formula (VI):

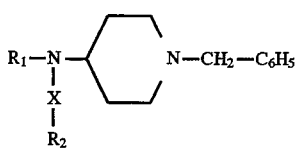

in which $R_1$, $R_2$ and X have the same meaning as in the formula (I), which is debenzylated by catalytic hydrogenation, hydrogen transfer (in the presence of ammonium formate) or by dealkylation (in the presence of chloroethyl-chloroformate), to lead to the compound of formula (VII):

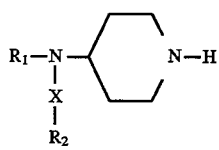

in which $R_1$, $R_2$ and X have the same meaning as in the formula (I), which is reacted with a compound of formula (VIII):

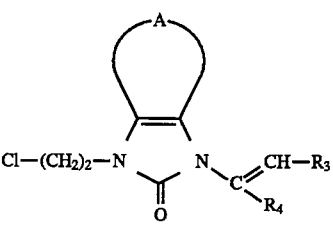

in which A, $R_3$ and $R_4$ have the same meaning as in the formula (I), to lead to the compound of formula (I), or a piperidine of formula (IX):

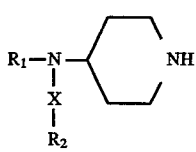

in which $R_1$, $R_2$ and X have the same meaning as in the formula (I), which is reacted with ethylene oxide, to lead to the compound of formula (X):

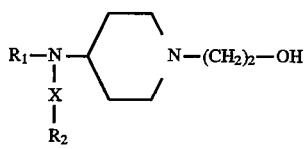

in which $R_1$, $R_2$ and X have the same meaning as in formula (I), which is reacted with thionyl chloride to lead to the compound of formula (XI):

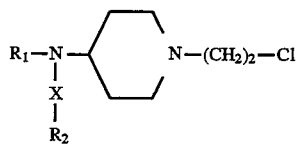

in which $R_1$, $R_2$ and X have the same meaning as in the formula (I), which is reacted with the compound of formula (XII):

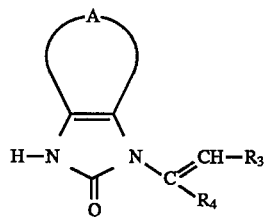

in which A, $R_3$ and $R_4$ are as defined in the formula (I), to lead to the compound of formula (I), which compound of formula (I):

can be, if appropriate, purified according to a conventional purification technique, is separated, if appropriate, into the isomers according to a conventional separation technique, is converted, if desired, into its addition salts with a pharmaceutically acceptable acid or into a quaternary ammonium salt of the piperidine.

The compounds of the invention have very advantageous pharmacological properties. They are specific ligands of neurokinin receptors which have, in particular, particularly intense antagonist properties with respect to $NK_1$ receptors. $NK_1$ receptors would be more particularly involved in the regulation of pain transmission, edema caused by increasing the vasopermeability, secretary phenomena in the tracheobronchial and gastrointestinal systems, salivation, control of breathing and vascular tonicity, and activation of the cells which participate in inflammatory processes.

Another subject of the present invention is pharmaceutical compositions containing, as active principle, at least one compound of formula (I), alone or in combination with one or a number of nontoxic inert excipients or vehicles.

Mention can more particularly be made, among the pharmaceutical compositions according to the invention, of those which are suitable for oral, parenteral or nasal administration, simple or sugar-coated tablets, sublingual tablets, gelatin capsules, lozenges, suppositories, creams, ointments, dermal gels, and the like.

The useful dose varies according to the age and the weight of the patient, the nature and the severity of the complaint and the administration route. The latter can be oral, nasal, rectal or parenteral. The unit dose generally ranges between 0.1 and 100 mg for a treatment administered 1 to 3 times per 24 hours.

The following examples illustrate the invention without limiting it in any way. The starting materials used are known products or products prepared according to known procedures.

The compounds described in Preparations A to M are synthetic intermediates which are useful in the preparation of the compounds of formula (I).

The chemical structures of the compounds described in the examples were determined using the usual spectroscopic techniques (proton and carbon-13 magnetic resonance, mass spectrum, and the like).

PREPARATION A 1-(2-Chloroethyl)-3-isopropenyl-2(3H)-benzimidazolone 200 mmol of 1-bromo-2-chloroethane and 55 mmol of potassium carbonate are added to 50 mmol of 1-isopropenyl-2(3H)-benzimidazolone in 150 ml of dimethylformamide. The whole mixture is kept stirring for 48 hours. It is then poured into ice-cold water and extracted with dichloromethane. The organic phases are washed with water, dried and evaporated. The residue is then taken up in ether. The ether phase is washed with 2N potassium hydroxide and then with water, dried and evaporated and leads to the expected product.

PREPARATION B

3-Isopropenyl-2(3H)-benzimidazolone 1 ml of a 47% potassium hydroxide solution and then 530 mmol of methyl acetoacetate in solution in 20 ml of xylene are added to 500 mmol of 2-aminoaniline in 150 ml of xylene heated to 120° C. The whole mixture is heated and the water/methanol mixture formed is removed by means of a Dean and Stark apparatus. The whole mixture is then brought to reflux for 3 hours. After cooling to 40° C., 83 ml of 47% potassium hydroxide and 55 ml of water are added. The alkaline aqueous phase is neutralized with acetic acid. The expected product then crystallizes; it is filtered off, washed with water and dried.

Melting point: 120° C.

PREPARATION C

3-(1-Cyclopentenyl)-2(3H)-benzimidazolone 100 mmol of 2-aminoaniline and 135 mmol of 2-ethoxycarbonylcyclopentanone in 50 ml of xylene are brought to reflux for 5 hours, the water and the ethanol formed being removed with the aid of a Dean and Stark apparatus. After cooling, the expected product crystallizes and it is then filtered, washed with xylene and then with hexane and then dried.

Melting point: 158°–160° C.

PREPARATION D

3-Isopropenyl-2(3H)-naphtho[2,3-d]imidazolone

The expected product is obtained according to the process described in Preparation C, from 2,3-diaminonaphthalene and ethyl acetoacetate.

Melting point: 200°–203° C.

PREPARATION E

3-Isopropenyl-5,6-dichloro-2(3H)-benzimidazolone 0.3 ml of 47% potassium hydroxide and 160 mmol of methyl acetoacetate in 20 ml of xylene are successively added to 150 mmol of 2-amino-4,5-dichloroaniline in 50 ml of xylene, stirred at 120° C. The whole mixture is brought to reflux for 4 hours, the water/methanol mixture formed being removed by means of a Dean and Stark apparatus. After addition of 26 ml of 47% potassium hydroxide and 17 ml of water, the aqueous phase is washed with xylene and then neutralized with acetic acid. The expected product crystallizes and is filtered off, washed and dried.

Melting point: 190°–195° C.

PREPARATION F

3-Isopropenyl-7-methyl-2(3H)-benzimidazolone

The expected product is obtained according to the process described in Preparation C, from 2-amino-3-methylaniline and ethyl acetoacetate.

Melting point: 195° C.

PREPARATION G

3-Isopropenyl-4-nitro-2(3H)-benzimidazolone 0.3 ml of 47% potassium hydroxide and then 115 mmol of methyl acetoacetate are added to 100 mmol of 2-amino-3-nitroaniline in 50 ml of xylene brought to 120° C. The whole mixture is brought to reflux for 4 hours and the water/methanol mixture formed is removed by means of a Dean and Stark apparatus. 18 ml of 47% potassium hydroxide and 200 ml of water are then added. The aqueous phase is washed with xylene, brought to pH=6 with 12N hydrochloric acid and then extracted with ethyl acetate and the expected product is purified by chromatography on a silica column, using a dichloromethane/methanol (95/5) mixture as eluent.

PREPARATION H

1-(2-Chloroethyl)-3-isopropenyl-2-oxo-3H-imidazo [5,4-b]pyridine

Stage A: 3-Isopropenyl-2-oxo-3H-imidazo[5,4-b] pyridine

The expected product is obtained according to the process described in Preparation C, from 2,3-diaminopyridine and ethyl acetoacetate and after separation of the two positional isomers by chromatography on a silica column, using a dichloromethane/ethanol (98/2) mixture as eluent.

Stage B: 1-(2-Chloroethyl)-3-isopropenyl-2-oxo-3H-imidazo[5,4-b]pyridine

The expected product is obtained according to the process described in Preparation A. Final extraction is carried out with ethyl acetate.

PREPARATION I

1-(2-Chloroethyl)-3-(1-phenylvinyl)-2(3H)-benzimidazolone

Stage A: 3-(1-Phenylvinyl)-2(3H)-benzimidazolone 100 mmol of 2-aminoaniline and 100 mmol of ethyl benzoylacetate are heated at 200° C. for 5 minutes. 100 ml of xylene are then added to the above mixture and the water/ethanol mixture is recovered using a Dean and Stark apparatus. After cooling, the expected product crystallizes; it is filtered off, washed with cyclohexane and dried.

Melting point: 168°–170° C.

Stage B: 1-(2-Chloroethyl)-3-(1-phenylvinyl)-2(3H)-benzimidazolone 100 mmol of potassium carbonate and 200 mmol of 1-bromo-2-chloroethane are added to 50 mmol of the compound described in the preceding stage in 150 ml of dimethylformamide. The mixture is heated for 24 hours at 90° C. After concentrating, the residue is taken up in water and extracted with ethyl acetate. The organic phase is washed with 2N potassium hydroxide and then with water, dried and evaporated. The expected product is obtained after purification of the residue by chromatography on a silica column, a dichloromethane/ethanol (99/1) mixture being used as eluent.

PREPARATION J

1-(2-Chloroethyl)-3-[1-(trifluoromethyl)vinyl]-2(3H)-benzimidazolone

Stage A: 3-[1-(Trifluoromethyl)vinyl]-2(3H)-benzimidazolone

The expected product is obtained according to the process described in Preparation C, from 2-aminoaniline and ethyl trifluoroacetylacetate.

Melting point: 138°–140° C.

Stage B: 1-(2-Chloroethyl)-3-[1-(trifluoromethyl)vinyl]-2 (3H)-benzimidazolone

The expected product is obtained according to the process described in Preparation A. Final extraction is carried out with ethyl acetate.

Melting point: 158°–160° C.

PREPARATION K 1-(2-Chloroethyl)-3-(sec-but-1-enyl)-2(3H)-benzimidazolone

Stage A: 3-(sec-But-1-enyl)-2(3H)-benzimidazolone

The expected product is obtained according to the process described in Preparation B, from 2-aminoaniline and methyl propionylacetate.

Stage B: 1-(2-Chloroethyl)-3-(sec-but-1-enyl)-2(3H)-benzimidazolone

The expected product is obtained according to the process described in Preparation A.

PREPARATION L 1-(2-Chloroethyl)-3-isopropenyl-2-oxo-3H-imidazo[4,5-b]pyridine The expected product is obtained according to the process described in Preparation H, after separation in Stage A of the two positional isomers.

PREPARATION M 1-(2-Chloroethyl)-3-(sec-but-2-enyl)-2(3H)-benzimidazolone

Stage A: 3-(sec-But-2-enyl)-2(3H)-benzimidazolone

The expected product is obtained according to the process described in Preparation B, from 2-aminoaniline and ethyl 2-methylacetoacetate.

Melting point: 95°–97° C.

Stage B: 1-(2-Chloroethyl)-3-(sec-but-2-enyl)-2(3H)-benzimidazolone

The expected product is obtained according to the process described in Preparation A.

PREPARATION N

Mixture of 3-isopropenyl-5-trifluoromethyl-2(3H)-benzimidazolone and of 3-isopropenyl-6-trifluoromethyl-2(3H)-benzimidazolone The mixture of positional isomers is obtained according to the process described in Preparation B, from 2-amino-4-trifluoromethylaniline and methyl acetoacetate.

EXAMPLE 1

1-{2-[4-(N-Propionyl-(3,4-dichlorophenyl)amino)piperidino]ethyl}-3-isopropenyl -2(3H)-benzimidazolone Stage B: 1-Benzyl-4-[(3,4-dichlorophenyl)amino]piperidine 190 mmol of 1-benzyl-4-piperidone, 240 mmol of 3,4-dichloroaniline, 0.02 g of PTSA and 200 ml of toluene are placed in a round-bottomed flask equipped with a reflux condenser and a Dean and Stark apparatus. The whole mixture is brought to reflux for 24 hours. After evaporation of the solvent, the residue is taken up in 500 ml of methanol and 450 mmol of sodium borohydride are progressively added. The whole mixture is kept stirring for two days. The expected product is obtained after concentration by filtration of the precipitate formed.

Melting point: 95° C.

Stage B: 1-Benzyl-4-[N-propionyl-(3,4-dichlorophenyl)amino]piperidine 12 mmol of the compound obtained in the preceding stage and 32 mmol of propionic anhydride are placed in 60 ml of anhydrous xylene. The whole mixture is brought to reflux for 20 hours. After cooling, the solution is treated with an aqueous ammonia solution (0.5N). The organic phase is then washed with water until neutral, dried and evaporated and leads to the expected product.

Stage C: 4-[N-Propionyl-(3,4-dichlorophenyl)amino]piperidine 4.2 mmol of the compound obtained in the preceding stage in 25 ml of dichloromethane are debenzylated in the presence of 4.6 mmol of-chloroethyl chloroformate, according to the process described in J.O.C., 49, 2081–2082, 1984.

Stage D: 1-{2-[4-(N-Propionyl-(3,4-dichlorophenyl)amino)piperidino]ethyl}-3-isopropenyl-2(3H)-benzimidazolone 4 mmol of the compound obtained in the preceding stage and 4 mmol of the compound described in Preparation A are placed in 30 ml of dimethylformamide in the presence of 4.4 mmol of potassium carbonate. The whole mixture is stirred at 100° C. for 18 hours. After cooling and filtration, the solvent is evaporated. The residue is taken up in a dichloromethane/water mixture. The organic phase is washed until neutral, dried and evaporated. The expected product is obtained after purification of the residue by chromatography on a silica column, a dichloromethane/ethanol (95/5) mixture being used as eluent.

Melting point: 156° C.

Elemental microanalysis:

|  | C % | H % | N % | S % |
| --- | --- | --- | --- | --- |
| Calculated | 62.28 | 6.03 | 11.17 | 14.14 |
| Found | 61.79 | 6.08 | 10.85 | 13.83 |

EXAMPLE 2 1-{2-[4-(N-Propionylanilino)-piperidino]ethyl}-3-isopropenyl-2(3H)-benzimidazolone Stage A: 1-(2-Hydroxyethyl)-4-(N-propionylanilino)piperidine A solution, cooled to 15° C., containing 100 mmol of ethylene oxide in toluene is added slowly to 100 mmol of 4-(N-propionylanilino)piperidine in solution in 100 ml of anhydrous methanol cooled to 15° C. After returning to room temperature and removal of the azeotrope formed by distillation, the expected product is obtained after evaporation to dryness.

Stage B: 1-(2-Chloroethyl)-4-(N-propionylanilino)piperidine 125 mmol of thionyl chloride, in solution in 30 ml of toluene, are added to 100 mmol of the compound obtained in the preceding stage in 200 ml of toluene. The whole mixture is brought to reflux for 2 hours. After cooling, the precipitate formed is filtered off, washed with toluene and then with ether and dried and leads to the expected product.

Stage C: 1-{2-[4-(N-Propionylanilino)piperidino]ethyl}-3-isopropenyl-2(3H)-benzimidazolone 7 mmol of the product obtained in the preceding stage, 7 mmol of the compound described in Preparation B and 2.1 g of potassium carbonate in 60 ml of dimethylformamide are brought to 85° C. for 20 hours. After cooling and evaporation of the solvent, the residue is taken up in ethyl acetate and washed with water. After evaporation of the organic phase, the expected product is obtained after purification of the residue by chromatography on a silica column, a dichloromethane/ethyl acetate (50/50) mixture being used as eluent.

Melting point: 136° C.

Elemental microanalysis:

|  | C % | H % | N % |
|---|---|---|---|
| Calculated | 72.19 | 7.46 | 12.95 |
| Found | 72.12 | 7.80 | 12.78 |

EXAMPLE 3

1-{2-[4-(N-Butyrylanilino)piperidino]ethyl}-3-isopropenyl-2(3H)-benzimidazolone

The expected product is obtained according to the process described in Example 2, 4-(N-propionylanilino)piperidine being replaced in Stage A by 4-(N-butyrylanilino)piperidine.

Elemental microanalysis:

|  | C % | H % | N % |
|---|---|---|---|
| Calculated | 72.62 | 7.67 | 12.55 |
| Found | 72.64 | 7.69 | 12.31 |

EXAMPLE 4

1-{2-[4-(N-Propionylanilino)piperidino]ethyl}-3-(1-cyclopentenyl)-2(3H)-benzimidazolone The expected product is obtained according to the process described in Example 2, the product described in Preparation C being used in Stage C.

Elemental microanalysis:

|  | C % | H % | N % |
|---|---|---|---|
| Calculated | 73.33 | 7.47 | 12.22 |
| Found | 72.86 | 7.44 | 11.98 |

EXAMPLE 5

1-{2-[4-(N-Propionylanilino)piperidino]ethyl}-3-isopropenyl-2(3H)-naphtho[2,3-d]imidazolone The expected product is obtained according to the process described in Example 2, the product described in Preparation D being used in Stage C.

Melting point: 173°–175° C.

Elemental microanalysis:

|  | C % | H % | N % |
|---|---|---|---|
| Calculated | 74.66 | 7.10 | 11.61 |
| Found | 74.93 | 7.04 | 11.41 |

EXAMPLE 6

1-{2-[4-(N-Propionylanilino)piperidino]ethyl}-3-isopropenyl-5,6-dichloro-2(3H)-benzimidazolone The expected product is obtained according to the process described in Example 2, the product described in Preparation E being used in Stage C.

Elemental microanalysis:

|  | C % | H % | N % | Cl % |
|---|---|---|---|---|
| Calculated | 62.28 | 6.03 | 11.17 | 14.14 |
| Found | 61.95 | 5.97 | 10.66 | 14.49 |

EXAMPLE 7

1-{2-[4-(N-Propionylanilino)piperidino]ethyl}-3-isopropenyl-7-methyl-2(3H)-benzimidazolone The expected product is obtained according to the process described in Example 2, the product described in Preparation F being used in Stage C.

Elemental microanalysis:

|  | C % | H % | N % |
|---|---|---|---|
| Calculated | 72.62 | 7.67 | 12.55 |
| Found | 71.85 | 7.79 | 12.43 |

EXAMPLE 8

1-{2-[4-(N-Propionylanilino)piperidino]ethyl}-3-isopropenyl-4-nitro-2(3H)-benzimidazolone The expected product is obtained according to the process described in Example 2, the product described in Preparation G being used in Stage C.

Mass spectrum: FAB-[M+H]$^+$: m/z=478

EXAMPLE 9

1-{2-[4-(N-Propionyl-(3methoxyphenyl)amino)piperidino]ethyl}-3-isopropenyl-2(3H)-benzimidazolone The expected product is obtained according to the process described in Example 1, 3-methoxyaniline being used in Stage A.

Elemental microanalysis:

|  | C % | H % | N % |
|---|---|---|---|
| Calculated | 70.10 | 7.41 | 12.11 |
| Found | 70.17 | 7.44 | 12.04 |

EXAMPLE 10

1-{2-[4-(N-Propionyl-(4-methylphenyl)amino)piperidino]ethyl}-3-isopropenyl-2(3H)-benzimidazolone The expected product is obtained according to the process described in Example 1, 4-methylaniline being used in Stage A.

Melting point: 110° C.
Elemental microanalysis:

|  | C % | H % | N % |
|---|---|---|---|
| Calculated | 72.62 | 7.67 | 12.55 |
| Found | 72.62 | 7.70 | 12.28 |

EXAMPLE 11

1-{2-[4-(N-Propionyl-(4-chlorophenyl)amino) piperidino]ethyl}-3-isopropenyl-2(3H)-benzimidazolone The expected product is obtained according to the process described in Example 1, 4-chloroaniline being used in Stage A.

Melting point: 128° C.
Elemental microanalysis:

|  | C % | H % | N % | Cl % |
|---|---|---|---|---|
| Calculated | 66.87 | 6.69 | 12.00 | 7.59 |
| Found | 66.72 | 6.72 | 11.81 | 7.96 |

EXAMPLE 12

1-{2-[4-(N-Propionyl-(3-chlorophenyl)amino) piperidino]ethyl}-3-isopropenyl-2(3H)-benzimidazolone The expected product is obtained according to the process described in Example 1, 3-chloroaniline being used in Stage A.

Melting point: 128° C.
Elemental microanalysis:

|  | C % | H % | N % | Cl % |
|---|---|---|---|---|
| Calculated | 66.87 | 6.69 | 12.00 | 7.59 |
| Found | 66.59 | 6.65 | 11.66 | 7.68 |

EXAMPLE 13

1-{2-[4-(N-Propionyl-(2-naphthyl)amino)piperidino]ethyl}-3-isopropenyl-2(3H)-benzimidazolone The expected product is obtained according to the process described in Example 1, 2-naphthylamine being used in Stage A.

Melting point: 118°–120° C.
Elemental microanalysis:

|  | C % | H % | N % |
|---|---|---|---|
| Calculated | 74.66 | 7.10 | 11.61 |
| Found | 74.13 | 6.94 | 11.50 |

EXAMPLE 14

1-{2-[4-(N-Propionyl-(4-fluorophenyl)amino) piperidino]ethyl}-3-isopropenyl-2(3H)-benzimidazolone The expected product is obtained according to the process described in Example 1, 4-fluoroaniline being used in Stage A.

Elemental microanalysis:

|  | C % | H % | N % |
|---|---|---|---|
| Calculated | 69.31 | 6.94 | 12.43 |
| Found | 69.51 | 6.86 | 12.13 |

EXAMPLE 15

1-{2-[4-(N-Propionyl-(4-(1-hydroxy-2,2,2-trifluoroethyl)phenyl)amino) piperidino]ethyl}-3-isopropenyl -2(3H)-benzimidazolone The expected product is obtained according to the process described in Example 1, 4-(1-hydroxy-2,2,2-trifluoroethyl) aniline being used in Stage A.

Elemental microanalysis:

|  | C % | H % | N % |
|---|---|---|---|
| Calculated | 63.38 | 6.27 | 10.56 |
| Found | 63.39 | 6.25 | 10.31 |

EXAMPLE 16

1-{2-[4-(N-Propionyl-(3,4-dichlorophenyl)amino) piperidino]ethyl}-3-isopropenyl-2-oxo-3H -imidazo [5,4-b]pyridine The expected product is obtained according to the process described in Example 1, the product described in Preparation H being used in Stage D.

Mass spectrum: chemical ionization/NH$_3$: [M+H]$^+$: m/z= 503

EXAMPLE 17

1-{2-[4-(N-Propionyl-(3,4-dichlorophenyl)amino) piperidino]ethyl}-3-(1-cyclopentenyl)-2(3H)-benzimidazolone The expected product is obtained according to the process described in Example 2, 4-[N-propionyl-(3,4-dichlorophenyl)amino]piperidine being used in Stage A and the product described in Preparation C being used in Stage C.

Melting point: 155°–157° C.
Elemental microanalysis:

|  | C % | H % | N % | Cl % |
|---|---|---|---|---|
| Calculated | 63.76 | 6.11 | 10.62 | 13.36 |
| Found | 63.29 | 6.02 | 10.17 | 13.44 |

EXAMPLE 18

1-{2-[4-(N-Propionyl-(3,4-dichlorophenyl)amino) piperidino]ethyl}-3-isopropenyl-2(3H)-naphtho[2,3-d]imidazolone The expected product is obtained according to the process described in Example 2, 4-[N-propionyl-(3,4-dichlorophenyl)amino]piperidine being used in Stage A and the product described in Preparation D being used in Stage C.

Melting point: 185°–190° C.

Elemental microanalysis:

|  | C % | H % | N % | Cl % |
|---|---|---|---|---|
| Calculated | 65.33 | 5.85 | 10.16 | 12.86 |
| Found | 64.72 | 5.89 | 9.96 | 13.62 |

EXAMPLE 19

1-{2-[4-(N-(Piperidinocarbonyl)-anilino)piperidino]ethyl}-3-isopropenyl-2(3H)-benzimidazolone Stage A: 1-Benzyl-4-[N-(piperidinocarbonyl)anilino]piper-idine 60 mmol of 1-benzyl-4-anilinopiperidine, in 50 ml of toluene, are added slowly to 200 mmol of a 20% phosgene solution cooled to 10° C. The whole mixture is stirred for 30 minutes and then brought to 80° C. for 2 hours. The precipitate formed is filtered off and washed with toluene and then with isopropyl ether. 52 mmol of the precipitate obtained above are added to 58 mmol of piperidine in 150 ml of toluene and the mixture is heated to 80° C. After cooling, the whole mixture is poured into 200 ml of water. The organic phase, washed with water, is then dried and evaporated and leads to the expected product, which crystallizes.

Melting point: 118°–119° C.

Stage B: 4-[N-(Piperidinocarbonyl)anilino]piperidine 100 mmol of ammonium formate and 1.8 g of palladium/charcoal are added to 50 mmol of the compound obtained in the preceding stage in 200 ml of methanol. The mixture is brought to reflux for 2 hours. The catalyst is filtered off and the filtrate evaporated. The residue is then taken up in 150 ml of 1N hydrochloric acid. The acidic aqueous phase is washed with ether and then basified with sodium hydroxide. After extracting with ether, washing the ether phase with a saturated sodium chloride solution, filtering and evaporating, the expected product is obtained in the form of a white solid.

Melting point: 125° C.

Stage C: 1-{2-[4-[N-(Piperidinocarbonyl)anilino]piperidino]ethyl}-3-isopropenyl-2(3H)-benzimidazolone The expected product is obtained according to the process described in Stage D of Example 1, from the compound described in the preceding stage.

Elemental microanalysis:

|  | C % | H % | N % |
|---|---|---|---|
| Calculated | 71.43 | 7.65 | 14.36 |
| Found | 70.91 | 7.78 | 13.64 |

EXAMPLE 20

1-{2-[4-(N-Methoxyacetyl-(3,4-dichlorophenyl)amino)piperidino]ethyl}-3-isopropenyl-2(3H)-benzimidazolone Stage A: This stage is identical to Stage A in Example 1.

Stage B: 1-Benzyl-4-[N-methoxyacetyl-(3,4-dichlorophenyl)amino]piperidine 12 mmol of methoxyacetyl chloride are added to 12 mmol of 1-benzyl-4-[(3,4-dichlorophenyl)amino]piperidine obtained in the preceding stage in 50 ml of anhydrous tetrahydrofuran (THF). The mixture is brought to reflux for 3 hours. After cooling, the expected product is obtained by filtering the precipitate, which is washed with THF and dried.

Stage C: 4-[N-Methoxyacetyl-(3,4-dichlorophenyl)amino]piperidine

The expected product is obtained according to the process described in Stage C of Example 1.

Stage D: 1-{2-[4-(N-Methoxyacetyl-(3, 4-dichlorophenyl)amino)piperidino]ethyl}-3-isopropenyl-2(3H)-benzimidazolone The expected product is obtained according to the process described in Stage D of Example 1.

Elemental microanalysis:

|  | C % | H % | N % | Cl % |
|---|---|---|---|---|
| Calculated | 60.35 | 5.84 | 10.83 | 13.70 |
| Found | 61.00 | 6.13 | 9.99 | 13.98 |

EXAMPLE 21

1-{2-[4-(N-Propionylanilino)piperidino]-ethyl}-3-(1-phenylvinyl)-2(3H)-benzimidazolone The expected product is obtained according to the process described in Example 1, aniline being used in Stage A and the product described in Preparation I being used in Stage D.

Elemental microanalysis:

|  | C % | H % | N % |
|---|---|---|---|
| Calculated | 75.28 | 6.93 | 11.33 |
| Found | 74.45 | 6.82 | 10.91 |

EXAMPLE 22

1-{2-[4-(N-Propionyl-(3,4-dichlorophenyl)amino)piperidino]ethyl}-3-[1-(trifluoromethyl)vinyl]2(3H)-benzimidazolone The expected product is obtained according to the process described in Example 1, the product described in Preparation J being used in Stage D.

Mass spectrum: Chemical Ionization $(NH_3):[M+H]^+$: m/z=555

EXAMPLE 23

1-{2-[4-(N-Propionyl-(3-chloro-4-methylphenyl)amino)piperidino]ethyl}-3-isopropenyl-2(3H)-benzimidazolone The expected product is obtained according to the process described in Example 1, 3-chloro-4-methylaniline being used in Stage A.

Melting point: 138°–140° C.

Elemental microanalysis:

|  | C % | H % | N % | Cl % |
|---|---|---|---|---|
| Calculated | 67.42 | 6.91 | 11.65 | 7.37 |
| Found | 67.67 | 6.88 | 11.41 | 7.56 |

EXAMPLE 24

1-{2-[4-(N-Propionyl-(3,4-dimethylphenyl)amino)piperidino]ethyl}-3-isopropenyl-2(3H)-benzimidazolone The expected product is obtained according to the process described in Example 1, 3,4-dimethylaniline being used in Stage A and a catalytic hydrogenation being carried out in Stage C in the presence of palladium/charcoal as catalyst.
Melting point: 138° C.
Elemental microanalysis:

|  | C % | H % | N % |
|---|---|---|---|
| Calculated | 73.01 | 7.88 | 12.16 |
| Found | 73.25 | 7.81 | 11.95 |

EXAMPLE 25

1-{2-[4-(N-Propionyl-(3,4-difluorophenyl)amino) piperidino]ethyl}-3-isopropenyl-2(3H)-benzimidazolone The expected product is obtained according to the process described in Example 1, 3,4-difluoroaniline being used in Stage A.
Melting point: 166° C.
Elemental microanalysis:

|  | C % | H % | N % |
|---|---|---|---|
| Calculated | 66.65 | 6.45 | 11.96 |
| Found | 66.18 | 6.42 | 11.66 |

EXAMPLE 26

1-{2-[4-(N-Propionyl-(3,4-dichlorophenyl)amino) piperidino]ethyl}-3-(sec-but-1-enyl)-2(3H)-benzimidazolone The expected product is obtained according to the process described in Example 1, the product described in Preparation K being used in Stage D.
Melting point: 131° C.
Elemental microanalysis:

|  | C % | H % | N % | Cl % |
|---|---|---|---|---|
| Calculated | 62.91 | 6.26 | 10.87 | 13.76 |
| Found | 62.19 | 6.27 | 10.35 | 13.62 |

EXAMPLE 27

1-{2-[4-(N-Acetyl-(3,4-dichlorophenyl)amino) piperidino]ethyl}-3-isopropenyl-2(3H)-benzimidazolone The expected product is obtained according to the process described in Example 1, acetic anhydride being used in Stage B.
Melting point: 174° C.
Elemental microanalysis:

|  | C % | H % | N % | Cl % |
|---|---|---|---|---|
| Calculated | 61.60 | 5.79 | 11.49 | 14.55 |
| Found | 61.73 | 5.88 | 11.16 | 14.23 |

EXAMPLE 28

1-{2-[4-(N-Propionyl-(3,4-dichlorophenyl)amino) piperidino]ethyl}-3-isopropenyl-2-oxo-3H-imidazo[4,5-b]pyridine The expected product is obtained according to the process described in Example 1, the product described in Preparation L being used in Stage D.

Elemental microanalysis:

|  | C % | H % | N % | Cl % |
|---|---|---|---|---|
| Calculated | 59.76 | 5.82 | 13.94 | 14.11 |
| Found | 59.19 | 5.85 | 13.28 | 13.85 |

EXAMPLE 29

1-{2-[4-(N-Propionyl-(3,4-dichlorophenyl)amino) piperidino]ethyl}-3-(sec-but-2-enyl)-2(3H)-benzimidazolone The expected product is obtained according to the process described in Example 1, the product described in Preparation M being used in Stage D.

Mass Spectrum: Chemical ionization (NH$_3$): [M+H]$^+$: m/z=516

EXAMPLE 30

1-{2-[4-(N-Propionyl-(3,4-dimethoxyphenyl)amino) piperidino]ethyl}-3-isopropenyl-2-(3H)-benzimidazolone The expected product is obtained according to the process described in Example 1, 3,4-dimethoxyaniline being used in Stage A.

Melting point: 45° C.

Elemental microanalysis:

|  | C % | H % | N % |
|---|---|---|---|
| Calculated | 68.11 | 7.11 | 10.97 |
| Found | 68.27 | 7.37 | 11.37 |

EXAMPLE 31

1-{2-[4-(N-Propionyl-(pyrid-4-yl)amino)piperidino] ethyl}-3-isopropenyl-2(3H)-benzimidazolone The expected product is obtained according to the process described in Example 1, 4-aminopyridine being used in Stage A.

Melting point: 106° C.

Elemental microanalysis:

|  | C % | H% | N % |
|---|---|---|---|
| Calculated | 69.26 | 7.21 | 16.15 |
| Found | 69.33 | 7.26 | 16.00 |

EXAMPLE 32

1-{2-[4-(N-Propionyl-(3,4-dichlorophenyl)amino)
piperidino]ethyl}-3-isopropenyl-7-trifluoromethyl-2
(3H)-benzimidazolone Elemental microanalysis:

|  | C % | H % | N % | Cl % |
|---|---|---|---|---|
| Calculated | 56.95 | 5.13 | 9.84 | 12.45 |
| Found | 57.03 | 5.21 | 9.59 | 12.71 |

EXAMPLE 33

1-{2-[4-(N-Propionyl-(3,4-dichlorophenyl)amino)
piperidino]ethyl}-3-isopropenyl-5-trifluoromethyl-2
(3H)-benzimidazolone and

EXAMPLE 34

1-{2-[4-(N-Propionyl-(3,4-dichloro-phenyl)amino)
piperidino]ethyl}-3-isopropenyl -6-trifluoromethyl
-2(3H)-benzimidazolone The mixture of compounds was obtained according to the process described in Example 2, the product described in Preparation N being used in Stage C. The two compounds were then separated by chromatography on a silica column, a dichloro-methane/ethanol (98/2) mixture being used as eluent. The position of the trifluoromethyl groups was determined by proton NMR.

Example 33: Presence of a singlet on the phenyl ring situated at 7.25 ppm.

Example 34: Presence of a singlet on the phenyl ring situated at 7.60 ppm.

EXAMPLE 35

1-Methyl-1-[2-(3-isopropenyl-2-oxo-3H-
benzimidazol-1-yl)ethyl]-4-[N-propionyl-(3,4-
dichlorophenyl)amino]piperidinium iodide 424 mmol of the compound described in Example 1 and 500 mmol of methyl iodide are stirred in 25 ml of acetone for 5 days. The expected product is obtained by filtering the precipitate, dissolving in water and freeze-drying.

Mass spectrum: FAB:[M–I]$^+$: m/z=515

EXAMPLE 36

1-Methyl-1-[2-(3-isopropenyl-2-oxo-3H-
benzimidazol-1-yl)ethyl]4-(N-propionyl-anilino)
piperidinium iodide The expected product is obtained according to the process described in Example 35, from the compound described in Example 2.

Elemental microanalysis:

|  | C % | H % | N % | I % |
|---|---|---|---|---|
| Calculated | 56.45 | 6.14 | 9.75 | 22.09 |
| Found | 56.10 | 6.14 | 9.56 | 22.16 |

EXAMPLE 37

1-{2-[4-(N-Phthalimidoacetyl-(3-chloro-4-
methylphenyl)amino)piperidino]ethyl}-3-
isopropenyl-2(3H)-benzimidazolone The expected product is obtained according to the process described in Example 1, the corresponding starting materials being used.

Elemental microanalysis:

|  | C % | H % | N % | Cl % |
|---|---|---|---|---|
| Calculated | 66.71 | 5.60 | 11.44 | 5.79 |
| Found | 66.62 | 5.96 | 10.70 | 5.39 |

EXAMPLE 38

1-{2-[4-(N-Propionyl-(3,4-dichlorophenyl)amino)
piperidino]ethyl}-3-(1-phenylvinyl)-2(3H)-
benzimidazolone The expected product is obtained according to the process described in Example 1, 3,4-dichloroaniline being used in Stage A and the product described in Preparation I being used in Stage D.

Elemental microanalysis:

|  | C % | H % | N % | Cl % |
|---|---|---|---|---|
| Calculated | 66.07 | 5.72 | 9.94 | 12.58 |
| Found | 65.30 | 5.62 | 9.34 | 12.34 |

EXAMPLE 39

1-{2-[4-(N-Methoxyacetyl-(3,4-dichlorophenyl)
amino)piperidino]ethyl}-3-(1-cyclopentenyl)-2(3H)-
benzimidazolone The expected product is obtained according to the process described in Example 2, the product described in Preparation C being used in Stage C.

Melting point: 144°–145° C.

Elemental microanalysis:

|  | C % | H % | N % | Cl % |
|---|---|---|---|---|
| Calculated | 61.88 | 5.93 | 10.31 | 13.05 |
| Found | 62.08 | 6.09 | 9.95 | 12.99 |

EXAMPLE 40

1-{2-[4-(N-Piperidinocarbonyl-(3,4-dichlorophenyl)
amino)piperidino]ethyl}-3-isopropenyl-2(3H)-
benzimidazolone The expected product is obtained according to the process described in Example 1, the corresponding starting materials being used.

EXAMPLE 41

1-{2-[4-(N-Benzoyl-N-methylamino)piperidino] ethyl}-3-isopropenyl -2(3H)-benzimidazolone The expected product is obtained according to the process described in Example 1, the corresponding starting materials being used.

Melting point: 120°–122° C.

Elemental microanalysis:

|  | C % | H % | N % |
|---|---|---|---|
| Calculated | 71.71 | 7.22 | 13.30 |
| Found | 70.92 | 7.26 | 13.08 |

Elemental microanalysis:

|  | C % | H % | N % |
|---|---|---|---|
| Calculated | 62.59 | 6.34 | 12.58 |
| Found | 62.65 | 6.60 | 11.87 |

EXAMPLE 42

1-{2-[4-(N-Benzoyl-(3,4-dichlorophenyl)amino) piperidino]ethyl}-3-isopropenyl-2(3H)-benzimidazolone The expected product is obtained according to the process described in Example 1, the corresponding starting materials being used.

Melting point: 158° C. Elemental microanalysis:

|  | C % | H % | N % | Cl % |
|---|---|---|---|---|
| Calculated | 65.57 | 5.50 | 10.20 | 12.90 |
| Found | 65.15 | 5.55 | 9.82 | 13.37 |

EXAMPLE 43

1-{2-[4-(N-Propionyl-(2,5-dichlorophenyl)amino) piperidino]ethyl}-3-isopropenyl-2(3H)-benzimidazolone The expected product is obtained according to the process described in Example 1, the corresponding starting materials being used.

Melting point: 148° C.

Elemental microanalysis:

|  | C % | H % | N % | Cl % |
|---|---|---|---|---|
| Calculated | 62.28 | 6.03 | 11.17 | 14.14 |
| Found | 62.06 | 6.05 | 10.95 | 14.28 |

EXAMPLE 44

1-{2-[4-(N-Propionyl-(3-chloro-4-methoxyphenyl) amino) piperidino]ethyl}-3-isopropenyl-2(3H)-benzimidazolone The expected product is obtained according to the process described in Example 1, the corresponding starting materials being used.

Melting point: 150°–152° C.

Elemental microanalysis:

|  | C % | H % | N % | Cl % |
|---|---|---|---|---|
| Calculated | 65.25 | 6.69 | 11.27 | 7.13 |
| Found | 65.67 | 7.05 | 11.13 | 7.14 |

EXAMPLE 45

1-{2-[4-(N-Propionyl-(3-chloro-4-fluorophenyl) amino)piperidino]ethyl}-3-isopropenyl-2(3H)-benzimidazolone The expected product is obtained according to the process described in Example 1, the corresponding starting materials being used.

Melting point: 130°–132° C.

Elemental microanalysis:

|  | C % | H % | N % | Cl % |
|---|---|---|---|---|
| Calculated | 64.39 | 6.23 | 11.55 | 7.31 |
| Found | 64.24 | 6.26 | 11.45 | 7.34 |

EXAMPLE 46

1-{2-[4-(N-Propionyl-(2,4-dichlorophenyl)amino) piperidino]ethyl}-3-isopropenyl-2(3H)-benzimidazolone The expected product is obtained according to the process described in Example 1, the corresponding starting materials being used.

Elemental microanalysis:

|  | C % | H % | N % | Cl % |
|---|---|---|---|---|
| Calculated | 62.28 | 6.03 | 11.47 | 14.14 |
| Found | 61.59 | 6.12 | 10.88 | 14.69 |

EXAMPLE 47

1-{2-[4-(N-Propionyl-(3,5-dichlorophenyl)amino) piperidino]ethyl}-3-isopropenyl-2(3H)-benzimidazolone The expected product is obtained according to the process described in Example 1, the corresponding starting materials being used.

Melting point: 170° C.

Elemental microanalysis:

|  | C % | H % | N % | Cl % |
|---|---|---|---|---|
| Calculated | 62.28 | 6.03 | 11.17 | 14.14 |
| Found | 61.83 | 5.99 | 11.02 | 14.41 |

EXAMPLE 48

1-{2-[4-(N-Phthalimidoacetyl-(3,4-dichlorophenyl) amino)piperidino]ethyl}-3-isopropenyl-2(3H)-benzimidazolone The expected product is obtained according to the process described in Example 1, the corresponding starting materials being used.

EXAMPLE 49

1-{2-[4-(N-Aminoacetyl-(3,4-dichlorophenyl)amino)
piperidino]ethyl}-3-isopropenyl-2(3H)-
benzimidazolone The expected product is obtained by reaction of the compound described in Example 48 with hydrazine.

Melting point: 162° C.

Mass spectrum: FAB:[M+H]$^+$: m/z=502

EXAMPLE 50

1-{2-[4-(N-Aminoacetyl-(3-chloro-4-methylphenyl)
amino)piperidino]ethyl}-3-isopropenyl-2(3H)-
benzimidazolone The expected product is obtained by reaction of the compound described in Example 37 with hydrazine.

Melting point: 134° C.

Elemental microanalysis:

|            | C %   | H %  | N %   | Cl % |
|------------|-------|------|-------|------|
| Calculated | 64.79 | 6.69 | 14.53 | 7.35 |
| Found      | 63.67 | 6.62 | 14.05 | 7.56 |

Pharmacological study of the compounds of the invention

EXAMPLE 51

Affinity with Human $NK_1$ and $NK_2$ receptors

The affinity for human $NK_1$ and $NK_2$ receptors was studied on human IM-9 lymphoblasts expressing specifically the $NK_1$ receptor, as described by D. G. Payan et at. (J. Biol. Chem., 1986, 261, 14321–14329), and on CHO-K1 cells transfected with the $NK_2$ receptor according to the "CellPhect transfection" kit (Pharmacia).

The compounds of the invention showed an excellent specific affinity for the $NK_1$ receptors. Indeed, the Ki values of the compounds of the invention are between 0.7 and 11 nM whereas those observed for the $NK_2$ receptors are, for the lowest, of the order of a mole.

EXAMPLE 52

Tests on Isolated Smooth Muscle

In order to evaluate the functional activity of the compounds of the invention as neurokinin antagonists, three isolated smooth muscle preparations were used: rabbit vena cava (RVC), endothelium-free rabbit pulmonary artery (RPA) and rat portal vein (RPV), the contractile responses of which are respectively mediated by the $NK_1$, $NK_2$ and $NK_3$ receptors, as shown by D. Jukic et al. (Life Sci., 1991, 49, 1463–1469). The antagonist capacity of the compounds of the invention was expressed in the form of $pA_2$, as defined by O. Arunlakshana and H. O. Schild (Brit. J. Pharmacol., 1959, 14, 48–58). The compounds of the invention showed a powerful antagonist activity with respect to $NK_1$ receptors ($pA_2$ values of between 8.25 and 9.30) with a low activity for the $NK_2$ and $NK_3$ receptors ($pA_2$ values of between 5.00 and 6.75).

EXAMPLE 53

Study of the Antinociceptive Potential—Eddy Test in Mice

Due to the involvement of substance P in the nociceptive transmission in the spine (M. Otsuka and S. Konishi, TINS, 6, 317–320, 1983) and more particularly after thermal stimulation (A. W. Duggan et al., Brain Research, 1987, 403, 345–349), the in vivo pharmacological activity of the compounds of the invention was investigated in mice using the thermal hyperalgesia test originally described by N. B. Eddy et al. (J. Pharmacol., Exp. Ther., 1953, 107, 385–393). This test has been previously used to demonstrate the antinociceptive activity of antagonist substances for substance P of peptide nature (M. P. Piercey et al., Brain Research, 1986, 385, 74–85) and of non-peptide nature (A. Lecci et al., Neuroscience Letters, 1991, 129, 299–302). The experimental methodology is based on measuring the reaction time to heat, determined by licking the front paws, in mice (CD1 male, Ch. River, 25–30 g) placed on a metal plate heated to 55C. The animals were treated with the compounds of the invention intravenously at different times before being placed on the heating plate. The mean of the reaction times obtained for each batch treated (12 mice per batch) was compared with the mean of the corresponding control batch. The results are expressed in the form of $ED_{50}$ which corresponds to the dose which increases the reaction time by 50%. Whereas substance P, administered intraspinally, speeds up the reaction of the animal, the compounds of the invention slowed down this reaction time after intravenous injection. For example, the compound of Example 1 exerted a powerful activity, at a maximum 10 minutes after its iv administration, with an $ED_{50}$ of 0.79 g/kg.

EXAMPLE 54

Study of the Inhibition of Plasma Extravasation Induced By Substance P in Guinea Pigs The effect of the compounds on plasma extravasation caused by intravenous injection of substance P (1 g/kg) in guinea pigs was evaluated for the bladder, according to the method described for rats by C. Garret et al. (Proc. Natl. Acad. Sci., USA 1991, 88, 10208–20212). The accumulation in the bladder of Evan's blue, injected iv at the same time as the substance P and 10 minutes before sacrifice, was quantified spectrophotometrically after extraction of the dye with acetone. The inhibitory activity of the compounds administered intravenously 5 minutes before substance P was expressed as % of inhibition by comparison with a control batch (8 animals per batch). By way of example, the compound of Example 1 exerted a very good activity with an $ED_{50}$ of 0.16 mg/kg.

EXAMPLE 55

Study of the Inhibition of Broncho-Constriction Induced By Substance P in Guinea Pigs The study is carried out on male Hartley guinea pigs (Charles River) with a mean weight of 300 to 400 g. The study is carried out on anesthetized (ethyl carbamate 1.5 g/kg) and curarized (flaxedil 0.2 mg/kg iv) animals ventilated with a frequency of 60 per minute and a standard volume of 10 ml/kg. The animals are pretreated with pyrilamine (1 mg/kg iv), popranolol (1 mg/kg iv). The criterion for judging the bronchoconstriction is the increase in the tracheal insufflation pressure (TIP) induced by the injection of substance P by the iv route at the dose of 2 nm/kg iv, each animal being its own control. Injection of the tested product is carried out with respect to the time TO, injection of the product. The results are expressed as percentage of inhibition of the bronchoconstriction induced by substance P, this percentage being calculated according to the following formula:

(Δ TIP before product–Δ TIP after product)/Δ TIP before product (expressed as percentage).

During this test, the compound of Example 9 has a 50% inhibitory dose at the dose of 0.1 mg/kg iv.

Pharmaceutical Composition

EXAMPLE 56

Tablet: preparation formula for 1000 tablets, each containing a dose of 2 mg

| | |
|---|---|
| Compound of Example 1 | 2 g |
| Hydroxypropylcellulose | 2 g |
| Wheat starch | 10 g |
| Lactose | 100 g |
| Magnesium stearate | 3 g |
| Talc | 3 g |

We claim:
1. A compound selected from those of formula (I):

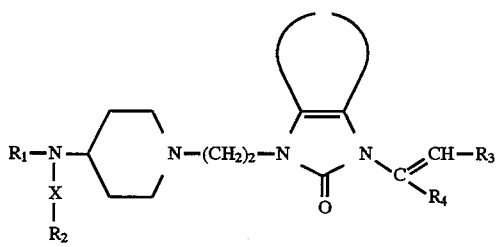

in which
$R_1$ represents linear or branched ($C_1$–$C_6$)alkyl, phenyl, naphthyl, pyridyl or thienyl, each phenyl, naphthyl, pyridyl, or thienyl optionally being substituted by one or a number of halogen or hydroxyl, linear or branched ($C_1$–$C_6$) alkoxy, linear or branched ($C_1$–$C_6$)alkyl, trihalomethyl, or 1-hydroxy-2,2,2-trifluoroethyl, $R_2$ represents hydrogen, linear or branched ($C_1$–$C_6$)alkyl (which is unsubstituted or substituted by one or a number of linear or branched ($C_1$–$C_6$)alkoxy or phenyl, amino, or phthalimido), phenyl (which is unsubstituted or substituted by one or a number of halogen or linear or branched ($C_1$–$C_6$)alkyl, linear or branched ($C_1$–$C_6$) alkoxy, hydroxyl, or trihalomethyl), cyclo($C_3$–$C_7$) alkyl, piperidino, or amino (which is unsubstituted or substituted by one or two linear or branched ($C_1$–$C_6$) alkyl), X represents CO or $SO_2$, $R_3$ represents hydrogen or linear or branched ($C_1$–$C_6$) alkyl, $R_4$ represents linear or branched ($C_1$–$C_6$)alkyl, phenyl (which is unsubstituted or substituted by one or a number of halogen or linear or branched ($C_1$–$C_6$)alkyl, linear or branched ($C_1$–$C_6$)alkyl, hydroxyl, or trihalomethyl) or trihalomethyl, or else $R_3$ and $R_4$ form, together with the carbon atoms which carry them, cyclo($C_3$–$C_7$)alkenyl, A represents, with the carbon atoms to which it is attached, a phenyl, naphthyl, or pyridyl ring, each phenyl, naphthyl, or pyridyl ring optionally being substituted by one or a number of halogen or linear or branched ($C_1$–$C_6$)alkyl, linear or branched ($C_1$–$C_6$) alkyl, hydroxyl, amino, nitro, or trihalomethyl, its isomers, corresponding quaternary ammonium salts, and its addition salts with a pharmaceutically-acceptable acid.

2. A compound of claim 1 in which X represents CO.

3. A compound of claim 1 in which $R_3$ represents hydrogen.

4. A compound of claim 1 in which $R_4$ represents linear or branched ($C_1$–$C_6$)alkyl.

5. A compound of claim 1 in which A represents a phenyl ring optionally substituted by one or a number of halogen or linear or branched ($C_1$–$C_6$)alkyl, linear or branched ($C_1$–$C_6$) alkoxy, hydroxyl, amino, nitro, or trihalomethyl.

6. The compound of claim 1 which is 1-{2-[4-(N-propionyl-(3,4-dichlorophenyl)amino)piperidino]ethyl}-3-isopropenyl-2(3H)-benzimidazolone.

7. The compound of claim 1 which is 1-{2-[4-(N-methoxyacetyl-(3,4-dichlorophenyl)amino)piperidino]ethyl}-3-isopropenyl-2(3H)-benzimidazolone.

8. A pharmaceutical composition useful as an $NK_1$ receptor antagonist comprising as active principle an effective amount of a compound as claimed in claim 1, together with one or more pharmaceutically-acceptable excipients or vehicles.

9. A method of treating smooth muscle disorders and inflammation related thereto by antagonizing the $NK_1$ receptor comprising the step of administering a therapeutically-effective amount of a compound of claim 1 to an animal or human living body in need of such a treatment.

10. A method of treating pain and inflammation related thereto by antagonizing the $NK_1$ receptor comprising the step of administering a therapeutically-effective amount of a compound of claim 1 to an animal or human living body in need of such a treatment.

* * * * *

UNITED STATES PATENT AND TRADEMARK OFFICE
CERTIFICATE OF CORRECTION

PATENT NO. : 5,652,246
DATED : July 29 1997
INVENTOR(S) : G. Nanteuil, G. Remond, B. Portevin, J. Bonnet, E. Canet, G. Birrell Page 1 of 2

It is certified that error appears in the above-indentified patent and that said Letters Patent is hereby corrected as shown below:

Column 2, line 10: "alkyl," at the end of the line should read -- alkoxy, --. Page 2, line 14

Column 2, line 21: "alkyl," at the beginning of the line should read -- alkoxy, --. Page 2, line 21

Column 13, line 16: "60 mmol of 1-benzyl-4-anilinopiperidine, ....." should begin a new paragraph. Page 16, line 4.

Column 16, line 36 (approx.): "Melting point 45°C" should read -- Melting point 145°C --. Page 20, line 6

Column 23, line 23 (approx.): In formula (I), the "A" is missing at the top. Page 28, line 2

Column 23, line 35: Insert a -- , -- (comma) after the word "pyridyl". Page 1 of Preliminary Amendment dtd 10/20/95, Claim 1, line 5.

UNITED STATES PATENT AND TRADEMARK OFFICE
CERTIFICATE OF CORRECTION

PATENT NO. : 5,652,246
DATED : July 29 1997
INVENTOR(S) : G. Nanteuil, G. Remond, B. Portevin, J. Bonnet, E. Canet, G. Birrell It is certified that error appears in the above-indentified patent and that said Letters Patent is hereby corrected as shown below:

Column 24, line 6: "alkyl," in the middle of the line, should read -- alkoxy, --. Page 28, line 19

Column 24, line 15: "alkyl," at the beginning of the line, should read -- alkoxy, --. Page 28, line 25

Signed and Sealed this

Twenty-first Day of October 1997

Attest:

BRUCE LEHMAN

Attesting Officer

Commissioner of Patents and Trademarks